United States Patent
Wailes et al.

(10) Patent No.: US 11,678,665 B2
(45) Date of Patent: *Jun. 20, 2023

(54) PYRAZINE-4-CARBAMATE OR -UREA DERIVATIVES AS HERBICIDES

(71) Applicant: Syngenta Participations AG, Basel (CH)

(72) Inventors: Jeffrey Steven Wailes, Bracknell (GB); Neil Brian Carter, Bracknell (GB); John Martin Clough, Bracknell (GB); John Williams, Bracknell (GB)

(73) Assignee: Syngenta Participations AG, Basel (CH)

( * ) Notice: Subject to any disclaimer, the term of this patent is extended or adjusted under 35 U.S.C. 154(b) by 349 days.

This patent is subject to a terminal disclaimer.

(21) Appl. No.: 16/649,621

(22) PCT Filed: Sep. 18, 2018

(86) PCT No.: PCT/EP2018/075230
§ 371 (c)(1),
(2) Date: Mar. 20, 2020

(87) PCT Pub. No.: WO2019/057724
PCT Pub. Date: Mar. 28, 2019

(65) Prior Publication Data
US 2020/0267983 A1    Aug. 27, 2020

(30) Foreign Application Priority Data
Sep. 22, 2017   (GB) .................................. 1715413

(51) Int. Cl.
| A01N 65/08 | (2009.01) |
| A01N 25/30 | (2006.01) |
| A01N 65/40 | (2009.01) |
| A01N 43/60 | (2006.01) |
| C07D 401/04 | (2006.01) |

(52) U.S. Cl.
CPC ............ *A01N 43/60* (2013.01); *C07D 401/04* (2013.01)

(58) Field of Classification Search
CPC .............................. A01N 43/60; C07D 401/04
See application file for complete search history.

(56) References Cited

U.S. PATENT DOCUMENTS
9,241,489 B2    1/2016   Jung et al.

FOREIGN PATENT DOCUMENTS

| JP | 06192252 A | 7/1994 | |
| JP | 2014-531438 A | 11/2014 | |
| JP | 2014208631 A | 11/2014 | |
| JP | 2015147757 A | 8/2015 | |
| WO | 2010141275 A1 | 12/2010 | |
| WO | WO-2015061247 A2 * | 4/2015 | ......... A61K 31/4409 |
| WO | 2017162524 A1 | 9/2017 | |

OTHER PUBLICATIONS

Gardner, D. Turf Magazine, "Summer Grassy & Broadleaf Weed". Jul. 1, 2014. Retrieved from URL: <https://turfmagazine.com/lawn-care/summer-grassy-broadleaf-weed-control/> on Apr. 29, 2022. (Year: 2014).*
Numata et al. (JP2014-208631A, cited in the IDS), Machine Translated. (Year: 2014).*
Numata et al. (JP2015-147757A, cited in IDS), Machine Translated (Year: 2015).*
Dolezal et al., Synthesis and Evaluation of Pyrazine Derivatives with Herbicidal Activity, Herbicides, Theory and Applications, Jan. 2011, InTech Europe, pp. 581-611.
International Search Report for International Patent Application No. PCT/EP2018/075230, dated Nov. 22, 2018.
GB Search Report for GB Patent Application No. GB1715413.9 date of search May 22, 2018.
Registry (STN); CAS Registration No. 1297656 to 13-3; May 20, 2011; 1 page.

* cited by examiner

*Primary Examiner* — Mina Haghighatian
*Assistant Examiner* — Janice Y Silverman
(74) *Attorney, Agent, or Firm* — BakerHostetler; Toni-Junell Herbert

(57) ABSTRACT

The present invention relates to herbicidal) active pyridyl-/pyrimidyl-pyrazine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

10 Claims, No Drawings

PYRAZINE-4-CARBAMATE OR -UREA DERIVATIVES AS HERBICIDES

CROSS-REFERENCE TO RELATED APPLICATIONS

This application is a 371 National Stage application of International Application No. PCT/EP2018/075230 filed Sep. 18, 2018 which claims priority to GB 1715413.9, filed Sep. 22, 2017, filed in the United Kingdom, the entire contents of which applications are hereby incorporated by reference.

The present invention relates to herbicidally active pyridyl-/pyrimidyl-pyrazine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Both WO2010/141275 and WO2010/071837 describe pyridyl-pyrazinecarboxylic acid derivatives for pharmaceutical use.

Certain pyridyl-pyrazine and pyrimidyl-pyrazine derivatives are known from JP2015-147757, where they are stated to have activity as insecticidal agents, and in particular acaricidal agents.

The present invention is based on the finding that pyridyl-pyrazine and pyrimidyl-pyrazine derivatives of Formula (I) as defined herein, exhibit surprisingly good herbicidal activity. Thus, in a first aspect of the invention there is provided a compound of formula (I)

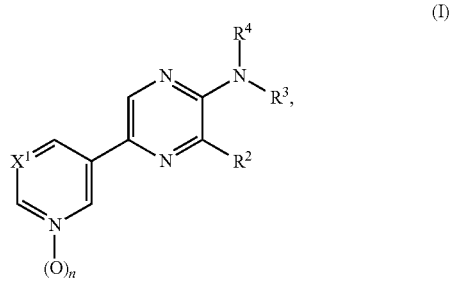

(I)

or a salt thereof, wherein:

$X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)O$C_1$-$C_6$alkyl, —S(O)$_p$$C_1$-$C_6$alkyl, N$R^6R^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, trimethylsilyl$C_2$-$C_6$alkynyl-, $C_3$-$C_6$cycloalkyl, $C_5$-$C_6$cycloalkenyl, —C(O)O$C_1$-$C_6$alkyl, —S(O)$_p$($C_1$-$C_6$alkyl), $C_1$-$C_6$alkoxy, $C_1$-$C_6$haloalkoxy, —O—$(CR^aR^b)_q$$R^{10}$, or phenyl;

$R^3$ is —C(O)$R^9$;

$R^4$ is selected from the group consisting of hydrogen, $C_1$-$C_6$alkyl, $C_1$-$C_6$haloalkyl, $C_2$-$C_6$alkenyl, $C_2$-$C_6$alkynyl, $C_r$alkoxy$C_s$alkyl, —$C_r$alkoxy$C_s$haloalkyl, $C_r$alkoxy$C_s$thioalkyl, —C(O)$R^9$ and —$(CR^aR^b)_q$$R^5$;

each $R^a$ is independently hydrogen or $C_1$-$C_2$ alkyl;
each $R^b$ is independently hydrogen or $C_1$-$C_2$ alkyl;

$R^5$ is —C(O)O$C_1$-$C_6$alkyl, —$C_3$-$C_6$cycloalkyl, cyano, —N$R^6R^7$, —C(O)N$R^aR^b$, —S(O)$_p$($R^{11}$)$_n$, -aryl or -heteroaryl wherein said aryl and heteroaryl are optionally substituted by 1 to 3 independent $R^8$;

$R^6$ and $R^7$ are independently selected from the group consisting of hydrogen, $C_1$-$C_6$alkyl and —C(O)O$C_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$($C_1$-$C_6$alkyl);

each $R^9$ is independently selected from the group consisting of hydrogen, $C_1$-$C_6$alkyl, $C_r$alkoxy$C_s$alkyl, $C_1$-$C_6$haloalkyl, $C_r$alkoxy$C_s$haloalkyl, $C_2$-$C_6$alkenyl, $C_2$-$C_6$alkynyl, and —$(CR^aR^b)_q$$R^{10}$;

or $R^4$ and $R^9$ together with the atoms to which they are joined form a 5-7 membered ring system containing from 1 to 3 heteroatoms, wherein at least one heteroatom is N, and any additional heteroatom is independently selected from S in the form of $S(O)_p$, O and N;

each $R^{10}$ is independently —C(O)O$R^c$, —OC(O)$R^c$, —$C_3$-$C_6$cycloalkyl, or an -aryl, -aryloxy, -heteroaryl, -heteroaryloxy or -heterocyclyl ring, wherein said ring is optionally substituted by 1 to 3 independent $R^8$;

$R^c$ is hydrogen or $C_1$-$C_4$alkyl;

each n is independently 0 or 1;

p is 0, 1, or 2;

each q is independently 0, 1, 2, 3, 4, 5 or 6;

r is 1, 2, 3, 4, or 5, s is 1, 2, 3, 4, or 5, and the sum of r+s is less than or equal to 6; and $R^{11}$ is $C_1$-$C_6$alkyl.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl, prop-3-enyl (allyl), ethynyl, prop-3-ynyl (propargyl), or prop-1-ynyl. Preferably, the term cycloalkyl refers to cyclopropyl, cyclobutyl, cyclopentyl or cyclohexyl.

In the context of the present specification the term "aryl" preferably means phenyl.

Heteroaryl groups and heteroaryl rings (either alone or as part of a larger group, such as heteroaryl-alkyl-) are ring systems containing at least one heteroatom and can be in mono- or bi-cyclic form. Preferably, single rings will contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Where appropriate compounds of formula (I) may also be in the form of/used as an N-oxide.

Compounds of formula (I) may also be in the form of/used as hydrates which may be formed during the salt formation.

Preferred values of $X^1$, $R^1$, $R^2$, $R^3$, $R^4$, $R^5$, $R^6$, $R^7$, $R^8$, $R^9$, $R^{10}$, $R^{11}$, $R^a$, $R^b$, $R^c$, n, p, q, r, and s are as set out below, and a compound of formula (I) according to the invention may comprise any combination of said values. The skilled person will appreciate that values for any specified set of embodiments may combined with values for any other set of embodiments where such combinations are not mutually exclusive.

The skilled man will appreciate that the values or r and s in the definitions $C_r$alkoxy$C_s$alkyl, $C_r$alkoxy$C_s$thioalkyl, and $C_r$alkoxy$C_s$haloalkyl are such that the length of the carbon chain within the substituent does not exceed 6. Preferred values of r are 1, 2, or 3. Preferred values for s are 1, 2, or 3. In various embodiments r is 1, s is 1; or, r is 1, s is 2; or r is 1, s is 3; or r is 2, s is 1; r is 2, s is 2; or r is 2, s is 3; or r is 3, s is 1; or r is 3, s is 2, r is 3, s is 3. Particularly preferred substituents thus include methoxymethyl, methoxybutyl, and ethoxymethyl, as well as methylthiomethyl and ethyl thiomethyl.

In one particular embodiment of the present invention, $X^1$ is N.

In another embodiment of the present invention, $X^1$ is $CR^1$. $R^1$ is preferably halogen or cyano, more preferably fluoro, chloro or cyano.

Most preferably $X^1$ is N or CF.

Preferably $R^2$ is halogen, cyano, $C_1$-$C_6$alkyl or $C_1$-$C_6$haloalkyl. More preferably $R^2$ is cyano, methyl or trifluoromethyl, Even more preferably $R^2$ is methyl or trifluoromethyl. Most preferably $R^2$ is trifluoromethyl.

Examples of preferred $R^3$ groups for use in the invention may be derived from the preferences for $R^9$ and the definitions therein. Particularly preferred $R^3$ groups are as defined within Table 1 below.

Preferably $R^4$ is selected from the group consisting of hydrogen, $C_1$-$C_4$alkyl, $C_3$-$C_6$alkenyl, $C_r$alkoxy$C_s$alkyl, $C_r$alkylthio$C_s$alkyl, $C_3$-$C_6$alkynyl, $C_1$-$C_3$haloalkyl, $C_r$alkoxy$C_s$haloalkyl, —C(O)$R^9$, and $(CR^aR^b)_qR^5$. More preferably $R^4$ is hydrogen, $C_1$-$C_4$alkyyl, $C_1$-$C_3$haloalkyl or —C(O)$R^9$. In one set of embodiments, $R^4$ is hydrogen or methyl.

In a further set of embodiments, where $R^4$ is —C(O)$R^9$, it is preferred that said $R^9$ is $C_1$-$C_3$alkyl, $C_2$-$C_4$alkenyl, or —$(CR^aR^b)_qR^{10}$. More preferably when $R^4$ is —C(O)$R^9$, said $R^9$ is hydrogen, -methyl, ethyl, propyl (including cyclopropyl), butenyl, —$C_1$-$C_3$alkoxy$C_1$-$C_3$alkyl, or —$(CH_2)_2$C(O)O$R^c$.

Where $R^4$ is $(CR^aR^b)_qR^5$, in one set of embodiments, q is 1, 2, or 3; $R^a$ and $R^b$ are independently hydrogen, methyl or ethyl (preferably hydrogen), and $R^5$ is —C(O)N$R^aR^b$, —N$R^6R^7$, cyano, or —$C_3$-$C_6$cycloalkyl (e.g. cyclopropyl), -aryl (e.g. phenyl) or -heteroaryl (in particular a 5- or 6-membered heteroaryl, such as for example, thiazolyl, pyridyl, pyrimidinyl, pyridazinyl, pyrazinyl, or triazinyl ring), wherein said aryl and heteroaryl are optionally substituted by 1 to 3 independent $R^8$.

In such embodiments where $R^5$ is —C(O)N$R^aR^b$, $R^a$ and $R^b$ are preferably independently hydrogen, methyl or ethyl (more preferably methyl).

Where $R^5$ is an optionally substituted heteroaryl ring, it is particularly preferred that said ring is a pyridyl or thiazolyl ring.

In an alternative embodiment of the present invention, $R^4$ and $R^9$ together with the atoms to which they are joined form a 5-7 membered ring system containing from 1 to 3 heteroatoms, wherein at least one heteroatom is N, and any additional heteroatom is independently selected from S, O and N. Preferably said ring system is a 5- or 6-membered N-linked heterocyclic ring system, and more preferably it is a pyrrolidinone, pyrrolidinedione or piperidinone ring. The skilled man will appreciate that the $R^9$ in these embodiments derives from $R^3$.

Preferably each $R^a$ is independently hydrogen, methyl or ethyl, more preferably hydrogen or methyl.

Preferably each $R^b$ is independently hydrogen, methyl or ethyl, more preferably hydrogen or methyl.

Preferably each q is independently 0, 1, 2 or 3. The skilled man will appreciate that if q is 0 when $R^4$ is $(CR^aR^b)_qR^5$, then $R^4$ is equivalent to $R^5$. Similarly if q is 0 when $R^9$ is $(CR^aR^b)_qR^{10}$, then $R^9$ is equivalent to $R^{10}$.

Preferably each $R^c$ is hydrogen, methyl or ethyl.

In one preferred set of embodiments, $R^3$ is as defined supra and $R^4$ is hydrogen. In a further set of preferred embodiments, $R^3$ and $R^4$ are both —C(O)$R^9$, wherein $R^9$ is the same or different.

In one particular embodiment $R^6$ and $R^7$ are both hydrogen. In another embodiment $R^6$ is hydrogen and $R^7$ is $C_1$-$C_6$alkyl (e.g., methyl or ethyl). In another embodiment, $R^6$ and $R^7$ are both $C_1$-$C_6$alkyl, in particular both are methyl, or both are ethyl.

Where an aryl, aryloxy, heteroaryl, heteroaryloxy, or heterocyclic ring system is substituted by 1 to 3 independent $R^8$ as described herein, it is preferred that such ring system is substituted by 1 or 2 independent $R^8$, more preferably by 1 $R^8$. Preferably each $R^8$ is independently selected from halogen or $C_1$-$C_3$ alkyl, $C_1$-$C_3$haloalkyl. More preferably each $R^8$ is independently fluoro, chloro or methyl.

Preferably $R^9$ is $C_1$-$C_6$alkyl [preferably methyl, ethyl, propyl (in particular iso-propyl) or butyl (in particular n-butyl or tert-butyl)], $C_1$-$C_3$haloalkyl, $C_1$-$C_3$alkoxy$C_1$-$C_3$alkyl or $(CR^aR^b)_qR^{10}$.

$R^{10}$ is preferably —C(O)O$R^c$, —OC(O)$R^c$, cyclopropyl, cyclobutyl, cyclopentyl, cyclohexyl, or a ring system selected from phenyl, phenoxy, pyridinyl, pyrimidinyl, thiazolyl, and thiophenyl, wherein said ring system is optionally substituted by 1-3 independent $R^8$.

Table 1 below provides 12 specific examples of herbicidal compounds of Formula (I) for use according to the invention.

TABLE 1

Specific examples of compounds of Formula (I) for use in the invention wherein $X^1$, $R^2$, $R^3$ and $R^4$ are as shown below in the table

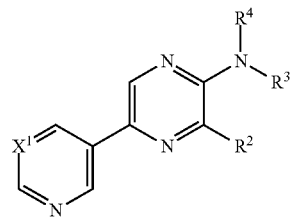

(I)

| Compound ID | $X^1$ | $R^2$ | $R^3$ | $R^4$ |
| --- | --- | --- | --- | --- |
| I1 | C—F | $CF_3$ | C(O)CH$_2$CH$_3$ | C(O)CH$_2$CH$_3$ |
| I2 | C—F | $CF_3$ | C(O)CH$_2$CH$_3$ | H |
| I3 | C—F | $CF_3$ | C(O)CH$_3$ | H |
| I4 | C—F | $CF_3$ | C(O)CH$_3$ | C(O)CH$_3$ |
| I5 | C—F | $CH_3$ | C(O)CH$_3$ | C(O)CH$_3$ |
| I6 | C—F | $CH_3$ | C(O)CH$_3$ | $CH_3$ |
| I8 | N | $CF_3$ | C(O)CH$_3$ | C(O)CH$_3$ |
| I9 | C—F | $CH_3$ | C(O)CH$_3$ | H |
| I10 | C—F | $CH_3$ | C(O)CH$_2$CH$_2$OCH$_3$ | H |
| I11 | C—F | $CF_3$ | C(O)CH$_2$CH$_2$OCH$_3$ | C(O)CH$_2$CH$_2$OCH$_3$ |
| I12 | N | $CF_3$ | C(O)CH$_2$CH$_3$ | C(O)CH$_2$CH$_3$ |

Compounds of Formula (I) may be prepared according to the following schemes, in which the substituents $X^1$, $R^1$, $R^2$, $R^3$, $R^4$, $R^5$, $R^6$, $R^7$, $R^8$, $R^9$, $R^{10}$, $R^{11}$, $R^a$, $R^b$, $R^c$, n, p, q, r, and s have (unless otherwise stated explicitly) the definitions described hereinbefore, using techniques known to the person skilled in the art of organic chemistry. General methods for the production of compounds of formula (I) are described below. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
Br. or br=broad
$^t$Bu=tert-butyl
t-BuOH=tert-butanol
d=doublet
dd=double doublet
DMF=N, N-dimethylformamide
DMSO=dimethylsulfoxide
DPPA=diphenylphosphoryl azide
Et$_3$N=triethylamine
Et$_2$O=diethyl ether
EtOAc=ethyl acetate EtOH=ethanol
HPLC=High Performance Liquid Chromatography
m=multiplet
Me=methyl
MeOH=methanol
Ph=phenyl
q=quartet
RT=room temperature
s=singlet
t=triplet
Tf=triflate
TFA=trifluoroacetic acid
THF=tetrahydrofuran
TMS=tetramethylsilane
tr=retention time.

Processes for preparation of compounds, e.g. a compound of formula (I) (which optionally can be an agrochemically acceptable salt thereof), are now described, and form further aspects of the present invention. A summary of approaches will be described first, and this will be followed by more detailed descriptions of some of the preferred approaches and transformations.

It will be understood by those skilled in the art that the various transformations by which the compounds of the invention can be prepared can be carried out in a variety of orders. For example, the bond between the two heterocycles can be made by a cross-coupling reaction, after which the groups $NR^3R^4$ and $R^2$ may be introduced or modified, or the cross-coupling reaction may be the final step in a sequence of reactions leading to the compounds of the invention.

The pyrazines of Formula (I) can be prepared by the following eight key steps:

(A) Linking the two heteroaromatic rings by cross-coupling. In one preferred approach, cross-coupling is a Suzuki reaction in which a 3-pyridyl- or 5-pyrimidinyl-boronic acid reacts with a halo-pyrazine, but either heterocycle can carry the required metallic (or quasi-metallic) functional group, and either can carry the complementary halogen or other leaving group, e.g. $OSO_2CF_3$.

(B) Regioselective introduction of functional groups to the pyrazine ring, e.g. bromination at the 5-position of a 2-amino-pyrazine, after which the new functional groups may be further modified.

(C) Formation of the group $NR^3R^4$, when it is $NH_2$, from a different functional group, e.g. by reduction of a nitro group or an azido group, by hydrolysis of an acylamino group, by Curtius rearrangement of a carboxyl group (and then hydrolysis if required), or by Hofmann rearrangement of a primary carboxamide (and then hydrolysis if required).

(D) Formation of the group $NR^3R^4$ in which at least one of the groups $R^3$ and $R^4$ is not hydrogen from a group $NR^3R^4$ in which at least one of the groups $R^3$ and $R^4$ is hydrogen, either by direct alkylation, for example, or by using reductive amination, or by acylation and then reduction of the resulting amide.

(E) Introduction of the group $NR^3R^4$ by displacement of a halogen or an alternative leaving group, e.g. $OSO_2CF_3$.

(F) Construction of the group $R^2$ from another group at the same position on the pyrazine ring, or by displacement of a leaving group at the same position on the pyrazine ring.

(G) N-Oxidation of the pyridine or pyrimidine ring.

(H) De novo synthesis of the pyrazine ring.

A more detailed description of some of the preferred transformations and approaches will now be given, all shown for compounds of the invention and intermediates in which n=0.

Compounds of Formula Ia are compounds of the invention of Formula (I) in which $R^4$ is not $C(O)R^9$, and compounds of Formula Ib are compounds of the invention of Formula (I) in which $R^4$ is $C(O)R^9$.

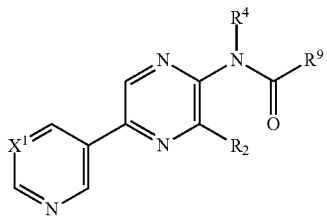

Formula Ia

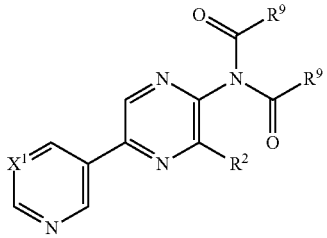

Formula Ib

A compound of Formula Ia can be prepared from a compound of Formula 1 using, for example, an acid of formula $R^9CO_2H$ and a suitable dehydrating reagent, an acid chloride of formula $R^9COCl$, optionally in the presence of a suitable base, or an anhydride of formula $(R^9CO)_2O$, in a suitable solvent in each case, as shown in Scheme 1.

Scheme 1

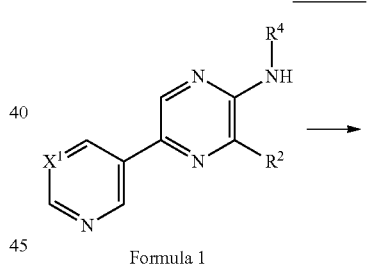

Formula 1

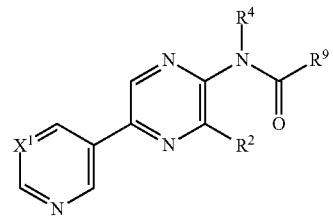

Formula Ia

If $R^4$ is H in the compound of Formula 1, acylation can take place either once or twice, leading either to a compound of the invention of Formula Ia in which $R^4$ is H, or to a compound of the invention of Formula 1b. Reaction conditions, including ratios of reactants, can be chosen to favour one or other of these two products. For examples of reactions of these types, see B S Bates et al., Bioorg. Med. Chem. Lett., 2014, 24, 3307, Y Qian et al., ACS Med. Chem. Lett., 2013, 4, 414, and V Karaluka et al., Org. Biomol. Chem., 2015, 13, 10888.

Scheme 2

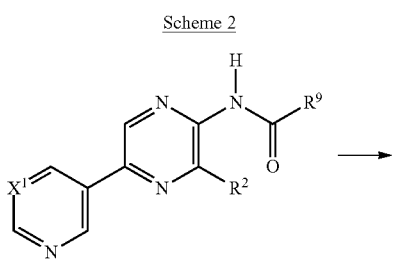

Formula Ia
R⁴ = H

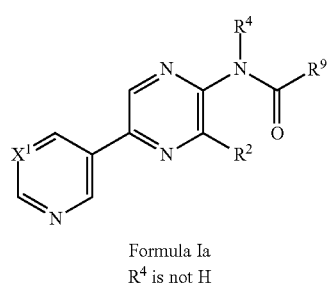

Formula Ia
R⁴ is not H

A compound of Formula Ia in which $R^4$ is not hydrogen can be prepared from a compound of Formula Ia in which $R^4$ is H, as shown in Scheme 2.

If $R^4$ is $C(O)R^9$ in the product of this reaction, the conversion can be carried out in the same way as described above in Scheme 1. If $R^4$ is alkyl, alkoxyalkyl, haloalkyl, haloalkoxyalkyl, cycloalkyl, allyl or propargyl in the product, the reaction can be carried out using a suitable reagent of formula $R^4$-LG, in which LG is a leaving group such as a halogen or $OSO_2CH_3$, optionally in the presence of a base, and in a suitable solvent (see, for example, International Patent Publication No. WO 2010/12747). Compounds of formula $R^4$-LG are commercially available or can be prepared by methods described in the literature.

A compound of Formula 1 in which $R^4$ is alkyl, alkoxyalkyl, haloalkyl, haloalkoxyalkyl, cycloalkyl, allyl or propargyl can be prepared from a compound of Formula 4 by treatment with a reagent $R^4$-LG, in which LG is a leaving group such as a halogen or $OSO_2CH_3$, optionally in the presence of a base, and in a suitable solvent, as shown in Scheme 3 (see, for example, P Jeanjot et al., Synthesis, 2003, 513).

Scheme 3

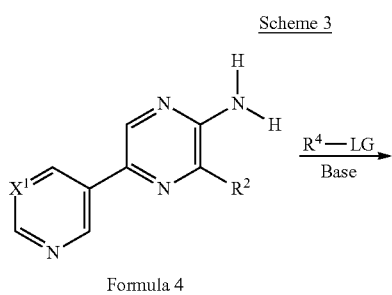

Formula 4

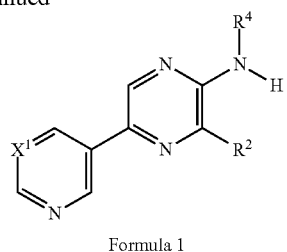

Formula 1

Compounds of formula $R^4$-LG are commercially available or can be prepared by methods described in the literature.

Amino-pyrazines can also be mono-methylated on the amino-group using methanol, sodium hydroxide and an iridium catalyst (see F Li et al., RSC Advances, 2012, 2, 8645). Related N-alkylations using other alcohols have also been reported (see, for example, S Li et al., Green Chem., 2015, 17, 3260).

In an alternative approach, a compound of Formula 1 in which $R^4$ is not hydrogen can be prepared from a compound of Formula 4 by reaction with an aldehyde $R^W$—CHO, in which $R^W$—$CH_2$=$R^4$, in the presence of a reducing agent, and in a suitable solvent, as shown in Scheme 4 (for examples, see P Jeanjot et al., Synthesis, 2003, 513). Ketones can also be used instead of the aldehyde $R^W$—CHO, and lead to branched substituents on the amino group (see, for example, International Patent Publication No. WO 2011/073149). Aldehydes of formula $R^W$—CHO and the corresponding ketones are commercially available or can be prepared by methods described in the literature.

Scheme 4

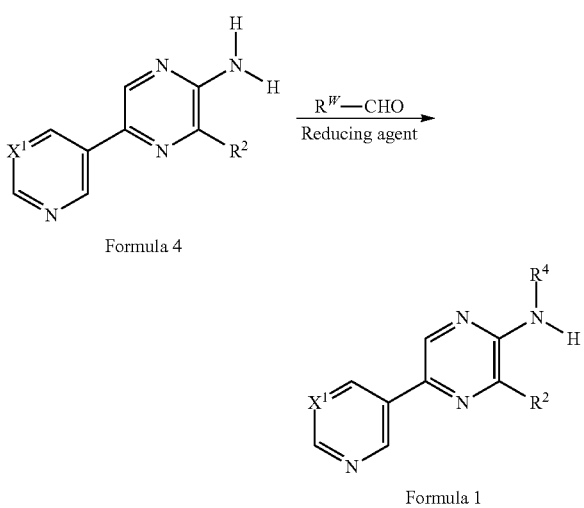

Amino-pyrazines can also be mono-alkylated (or mono-benzylated, etc.) by acylation at the amino-group and then reduction of the resulting amide using, for example, lithium aluminium hydride, in a suitable solvent (for examples, see P Jeanjot et al., Synthesis, 2003, 513).

In an alternative approach, a compound of Formula 1 may be prepared from a compound of Formula 5, in which W is a suitable halogen, such as Cl, Br or I, or another suitable leaving group, such as $OSO_2CF_3$, by reaction with an amine of formula $R^4NH_2$, optionally in the presence of a suitable catalyst and/or a suitable ligand and/or a suitable base, and in a suitable solvent, as shown in Scheme 5. For examples of reactions of this kind, see A J Henderson et al., Bioorg. Med. Chem. Letts., 2010, 20, 1137, and P J J Colbon et al., J. Het. Chem., 2008, 45, 1451. Amines of formula $R^4NH_2$ are commercially available or can be prepared by methods described in the literature.

Scheme 5

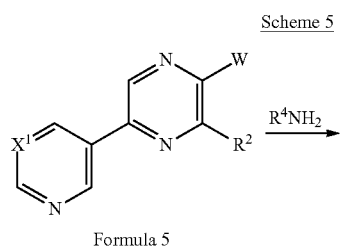

Formula 5

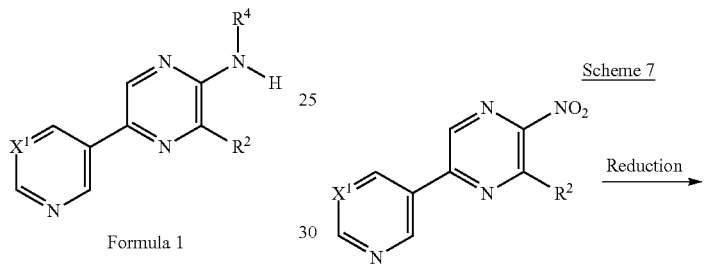

Formula 1

A compound of the invention of Formula Ia may also be prepared by reaction of a pyrazine of Formula 5, in which W is a suitable halogen, such as Cl, Br or I, or another suitable leaving group, such as $OSO_2CF_3$, with an amide of formula $R^9C(O)NHR_4$, optionally in the presence of a suitable catalyst and/or a suitable ligand and/or a suitable base, and in a suitable solvent, as shown in Scheme 6. For examples of reactions of this kind, see S Claerhout et al., Tetrahedron, 2012, 68, 3019. Amides of formula $R^9C(O)NHR_4$ are commercially available or may be prepared by methods described in the literature.

Scheme 6

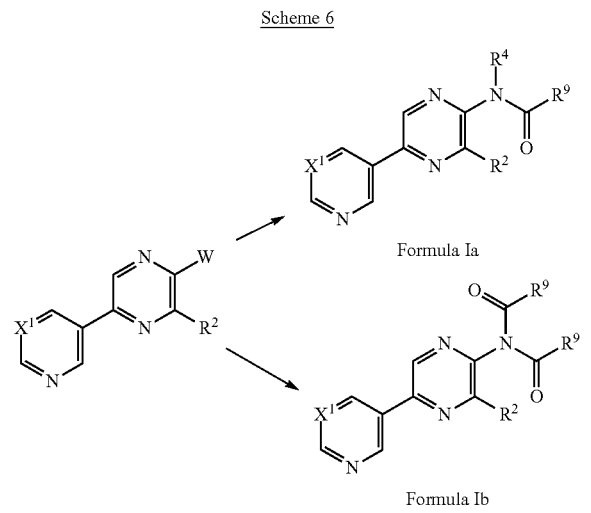

Formula Ia

Formula Ib

In a similar way, a compound of the invention of Formula Ib may be prepared by reaction of a pyrazine of Formula 5 with an imide of formula $(R^9CO)_2NH$, optionally in the presence of a suitable catalyst and/or a suitable ligand and/or a suitable base, and in a suitable solvent, as shown in Scheme 6. For related reactions, see E H Morkved, Chem. Het. Compounds, 2007, 43, 1197. Imides of formula $(R^9CO)_2NH$ are commercially available or may be prepared by methods described in the literature.

A compound of Formula 4 can be prepared by reduction of the corresponding nitro-compound, optionally in the presence of a catalyst, and in a suitable solvent, as shown in Scheme 7 (see, for example, International Patent Publication No. WO 2013/078254).

Similarly, a compound of Formula 4 can be prepared by reduction of the corresponding azide, optionally in the presence of a catalyst and in a suitable solvent (see, for example, N Sato et al., Synthesis, 1994, 931).

Scheme 7

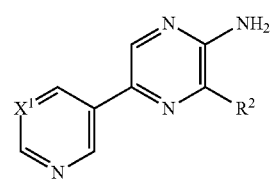

Reduction

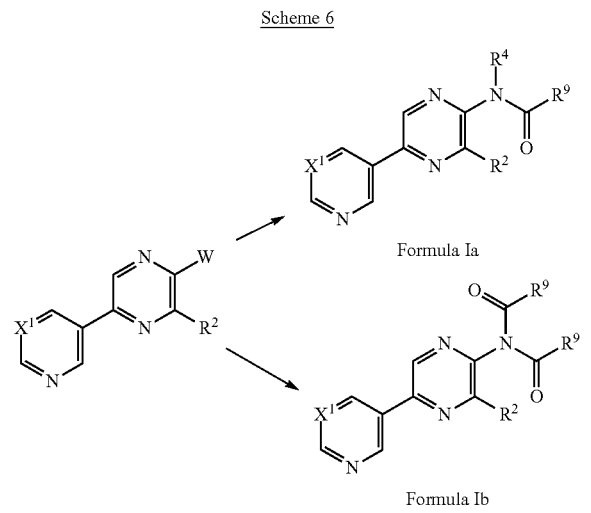

Formula 4

A compound of Formula 4 can also be prepared from a pyrazine carboxylic acid by Curtius rearrangement and then hydrolysis of the first-formed product, as shown in Scheme 8. For examples of Curtius reactions of this kind, see S Sunami and M Ohkubo, Tetrahedron, 2009, 65, 638, and M J I Andrews et al., Bioorg. Med. Chem. Lett., 2012, 22, 2266. The starting carboxylic acids shown in Scheme 8 can be prepared, for example, by hydrolysis of the corresponding methyl or ethyl esters. The same transformation can also be carried out using the Schmidt reaction or the Lossen rearrangement.

Scheme 8

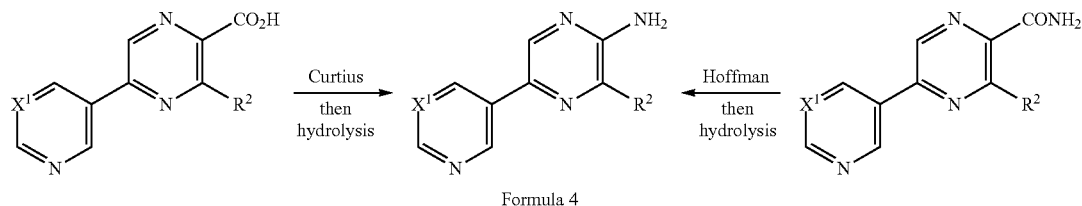

Formula 4

Similarly, a compound of Formula 4 can be prepared from a primary carboxamide by Hofmann rearrangement and then hydrolysis of the first-formed product (Scheme 8). See, for example, G Madhusudhan et al., Org. Chem.: An Indian Journal, 2009, 5, 274. The starting carboxamide shown in Scheme 8 can be prepared, for example, from the corresponding carboxylic acid via the acid chloride, or from the corresponding methyl or ethyl ester, or by partial hydrolysis of the corresponding cyanide.

A compound of the invention of Formula (I) can also be prepared by a cross-coupling reaction, as shown in Scheme 9. The cross-coupling partners can be a pyrazine of Formula 6, in which Y is chlorine, bromine, iodine or a pseudohalogen such as $OSO_2CF_3$, and a pyridine or pyrimidine of Formula 7, in which Q is the group $B(OR^Y)_2$ (this is preferred) or $Sn(R^Z)_3$ (in which $R^Y$=H or alkyl or the two groups $R^Y$ may join to form a ring, and $R^Z$=alkyl), in the presence of a suitable catalyst, usually a palladium catalyst, and optionally in the presence of a suitable ligand and/or a suitable base, and in a suitable solvent. Alternatively, the cross-coupling partners can be a pyrazine of Formula 6, in which Y is the group $B(OR^Y)_2$ (this is preferred) or $Sn(R^Z)_3$, and a pyridine or pyrimidine of Formula 7, in which Q is chlorine, bromine, iodine or a pseudohalogen such as $OSO_2CF_3$, in the presence of a suitable catalyst, usually a palladium catalyst, and optionally in the presence of a suitable ligand and/or a suitable base, and in a suitable solvent. For examples of cross-coupling reactions of the type shown in Scheme 9, see U.S. patent application publication No. 2010/0099684, J J Caldwell et al., Tetrahedron, 2012, 68, 9713, and K Chen et al., Tet. Letts., 2012, 53, 4873.

A pyrazine of Formula 6 can be prepared by functionalisation of a pyrazine of Formula 8, as shown in Scheme 10. For example, when Y=bromine, this can be carried out by bromination using bromine or N-bromosuccinimide, or when Y=iodine, this can be carried out by iodination using iodine or N-iodosuccinimide, or when Y=$B(OR^Y)_2$ this can be carried out by reaction of the corresponding pyrazine in which Y=bromine or iodine with $(R^YO)_2B—B(OR^Y)_2$ under palladium catalysis, in a suitable solvent in each case. For an example of a bromination of this kind, see International Patent Publication No. WO 2010/071837.

Scheme 10

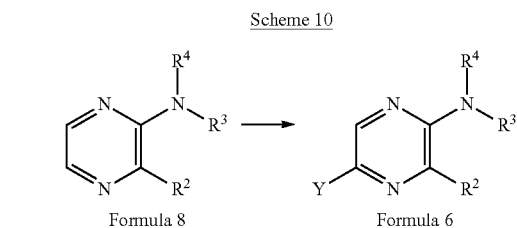

Formula 8      Formula 6

Pyridines and pyrimidines of Formula 7 are commercially available or can be made by methods described in the literature.

It will be understood by those skilled in the art that cross-coupling reactions of the types shown in Scheme 9 can also be carried out in a similar way on related pyrazines which, instead of $NR^3R^4$ and/or $R^2$, contain groups which are then converted into $NR^3R^4$ and/or $R^2$ after the cross-coupling reaction, using methods such as those shown in Schemes 1, 6 and 8. The group $NR^3R^4$ may also be modified after cross-coupling, using methods such as those shown in Scheme 2.

In an alternative approach, a compound of Formula (I) can be prepared from a compound of Formula 9 by the method shown in Scheme 11.

Scheme 9

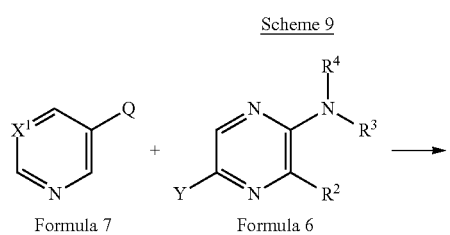

Formula 7     Formula 6

Formula (I)

Scheme 11

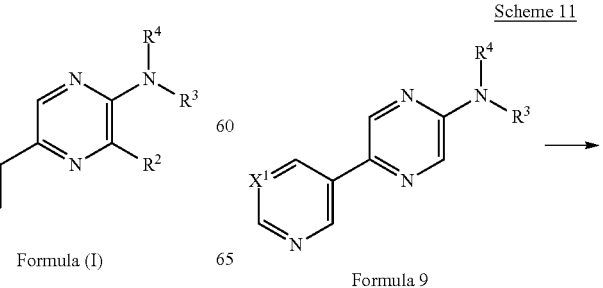

Formula 9

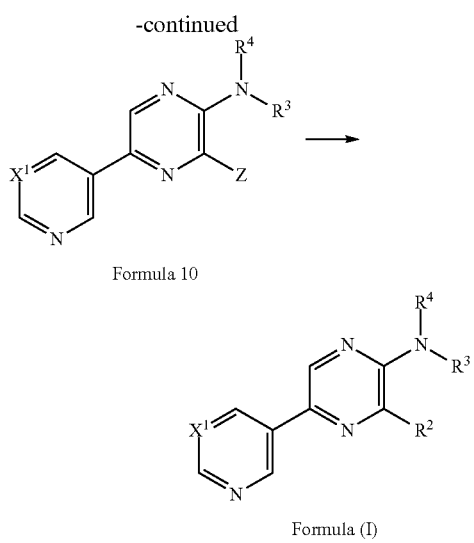

Formula 10

Formula (I)

In the first step, a group Z, which may be a halogen, alkylthio or nitro, is introduced directly to give a compound of Formula 10. For example, if Z=bromine, it can be introduced using bromine or N-bromosuccinimide, in a suitable solvent (see for example N Sato and R Takeuchi, Synthesis, 1990, 659). If Z is equal to a claimed value of $R^2$, this constitutes a way of directly introducing the group $R^2$ to prepare the corresponding compounds of the invention of Formula (I). Alternatively, the group Z can be converted in one or more steps by methods reported in the literature into the group $R^2$ to give a compound of the invention of Formula (I). For example, if the group Z is bromine, a substituent $R^2$ which is alkyl, cycloalkyl, alkenyl or aryl may be introduced by palladium-catalysed cross-coupling, and a substituent $R^2$ which is alkynyl may be introduced using a Sonogashira reaction, in a suitable solvent in each case.

Pyrazines of Formula 11, in which M is chlorine, bromine, iodine or a pseudohalogen such as $OSO_2CF_3$, and related compounds in which the group $NR^3R^4$ is replaced, for example, by $NH_2$ or NH-alkyl, can react regioselectively at the 3-position in displacement and cross-coupling reactions, as exemplified in Scheme 12. For example, the 3-bromo-group of 2-amino-3,5-dibromo-pyrazine is selectively displaced with alkoxides or secondary amines (see Examples 3-O and 3-P of International Patent Publication No. WO 2003/000666).

Scheme 12

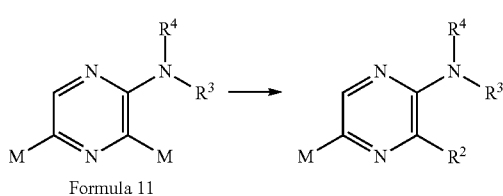

Formula 11

A compound of the invention of Formula (I) can also be prepared by approaches which involve the de novo synthesis of the pyrazine ring. A variety of such approaches have been reported in the literature. See, for example, Section 6.03.10 of Chapter 6.03, Pyrazines and their Benzo Derivatives, by N Sato, in Vol. 6 of Comprehensive Heterocyclic Chemistry II, Editors A R Katritzky, C W Rees and F V Scriven, Pergamon, 1996; N Sato, Science of Synthesis, 2004, 16, 751; and M P Cabal, Modern Heterocyclic Chemistry, 2011, 3, 1683. Representative examples of pyrazine ring syntheses are shown in Schemes 13 and 14 below.

Scheme 13

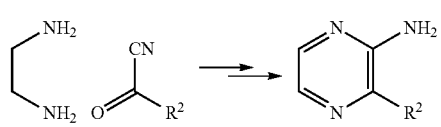

Scheme 13 shows the reaction of a 1,2-diamine with an acyl cyanide which leads, following oxidation, to 2-amino-3-substituted-pyrazines (see, for example, R Lakhan and B J Rai, Synthesis, 1987, 914). These can be converted to into compounds of the invention by methods described previously.

Scheme 14

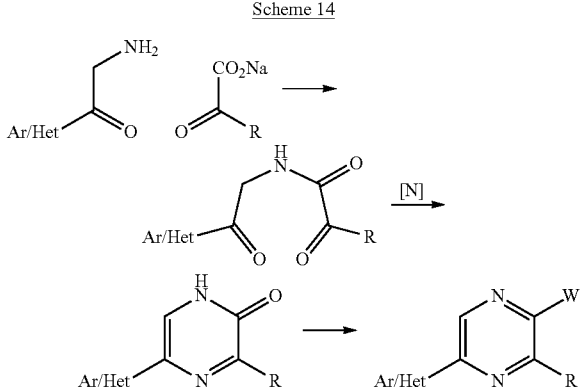

Scheme 14 shows a two-step approach to 3-substituted-5-aryl/heteroaryl-pyrazin-2-ones (see, for example, R H Bradbury et al., Heterocycles, 1990, 31, 1647). These pyrazin-2-ones can be converted, using methods reported in the literature, into the corresponding pyrazines with a group W at the 2-position, where W is a halogen, such as Cl, Br or I, or a group such as $OSO_2CF_3$. In turn, these pyrazines can be converted into compounds of the invention of Formula (I), as shown in Scheme 6.

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oeyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (1) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-gaffi* (English name "common barnyard grass", ECHCG), *Echinochloa oryzoides, Echinochloa colona* or *colonum, Eleusine indica, Eriochloa villosa* (English name "woolly cup-grass"), *Leptochloa chinensis, Leptochloa panicoides, Lolium perenne* (LOLPE, English name "perennial rye-grass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria*, and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. Where various intermediates described in said Examples are novel, these form yet further aspects of the invention. It will be appreciated that modification of detail may be made without departing from the scope of the invention.

PREPARATION EXAMPLES

Xantphos palladacycle 4th generation refers to methanesulfonato[9,9-dimethyl-4,5-bis(diphenylphosphino)xanthene](2'-methylamino-1,1'-biphenyl-2-yl)palladium(II) [1621274-19-8] see *Org. Lett.* 2014, 16, 4296 and WO13184198.

Example P1: Preparation of 2-(diacetylamino)-3-methyl-5-(5-fluoropyrid-3-yl)pyrazine (Compound I5)

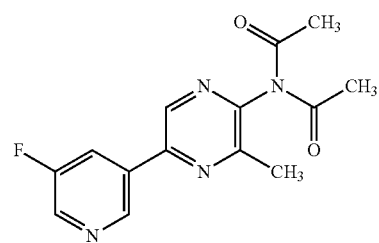 [SMILES: CC(=O)N(C(C)=O)c1ncc(-c2cncc(F)c2)nc1C]

Step 1: Preparation of 2-(diacetylamino)-3-methyl-5-(5-fluoropyrid-3-yl)pyrazine (Compound I5)

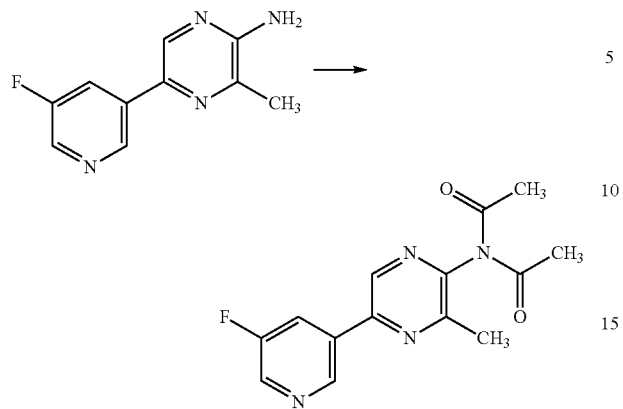

A mixture of 2-amino-3-methyl-5-(5-fluoropyrid-3-yl)pyrazine (190 mg, 0.93 mmol) and acetic anhydride (4 ml, 42 mmol) was heated for 30 minutes in the microwave at 100° C. After cooling, the mixture was diluted with toluene and excess acetic anhydride was removed by azeotropic distillation. The residue was purified by chromatography on silica gel using a gradient of ethyl acetate in isohexane as eluent to give 2-(diacetylamino)-3-methyl-5-(5-fluoropyrid-3-yl)pyrazine (200 mg, 75%) as a yellow solid.
$^1$H NMR (400 MHz, CDCl$_3$) δ9.10 (s, 1H), 8.90 (s, 1H), 8.60 (s, 1H), 8.15 (dd, 1H), 2.60 (s, 3H), 2.30 (s, 6H).

Example P2: Preparation of 2-(acetylamino)-3-trifluoromethyl-5-(5-fluoropyrid-3-yl)pyrazine (I3) and 2-(diacetylamino)-3-trifluoromethyl-5-(5-fluoropyrid-3-yl)pyrazine (I4)

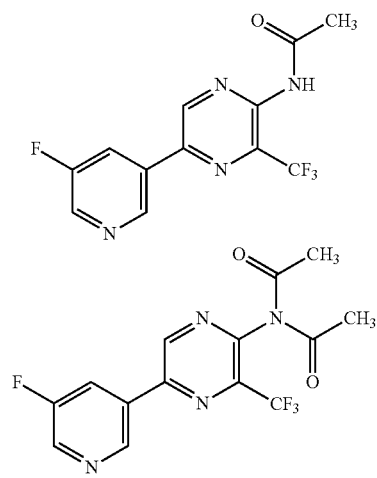

Step 1: Preparation of 2-(acetylamino)-3-trifluoromethyl-5-(5-fluoropyrid-3-yl)pyrazine (I3) and 2-(diacetylamino)-3-trifluoromethyl-5-(5-fluoropyrid-3-yl)pyrazine (I4)

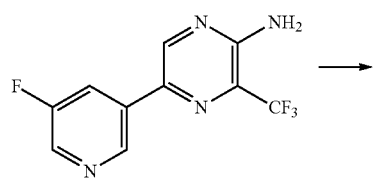

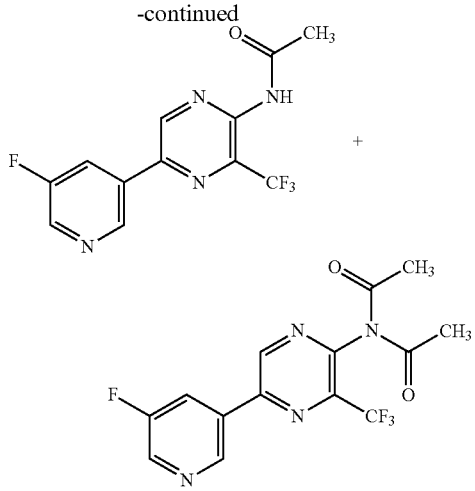

A mixture of 2-amino-3-trifluoromethyl-5-(5-fluoropyrid-3-yl)pyrazine (100 mg, 0.39 mmol) and acetic anhydride (2.0 ml, 21 mmol) was heated for 30 minutes in the microwave at 100° C., and then for a further 4 hours at 150° C. After cooling, the mixture was purified by mass directed reverse phase HPLC to give 2-(acetylamino)-3-trifluoromethyl-5-(5-fluoropyrid-3-yl)pyrazine (22 mg, 19%) and 2-(diacetylamino)-3-trifluoromethyl-5-(5-fluoropyrid-3-yl)pyrazine (40 mg, 30%) both as white solids.
I3: $^1$H NMR (400 MHz, CDCl$_3$) δ9.10 (s, 2H), 8.60 (s, 1H), 8.15 (dd, 1H), 7.85 (br s, 1H), 2.45 (s, 3H)
I4: $^1$H NMR (400 MHz, CDCl$_3$) δ9.30 (s, 1H), 9.15 (s, 1H), 8.70 (s, 1H), 8.25 (dd, 1H), 2.35 (s, 6H)

Example P3: Preparation of 2-amino-3-trifluoromethyl-5-(5-fluoropyrid-3-yl)pyrazine

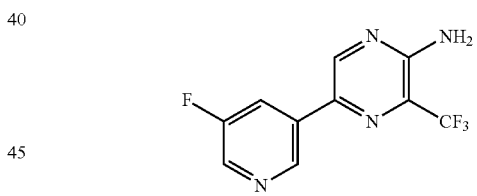

Step 1: Preparation of 2-amino-3-trifluoromethyl-5-(5-fluoropyrid-3-yl)pyrazine

2-Amino-3-trifluoromethyl-5-bromopyrazine (3.2 g, 13 mmol), (5-fluoro-3-pyridyl)boronic acid (2.6 g, 19 mmol) and Xantphos Palladacycle G4 (570 mg, 0.60 mmol) were dissolved in a mixture of toluene (64 ml), ethanol (16 ml) and aqueous potassium carbonate (2M, 13 ml) and the resulting mixture was heated under reflux for 2 hours and then allowed to cool. Volatiles were removed under reduced pressure and the resulting brown solid was dissolved in ethyl acetate then washed with water, dried over magnesium sulfate and concentrated under reduced pressure. The residue was purified by chromatography on silica gel using a gradient of ethyl acetate in isohexane as eluent to give 2-amino-3-trifluoromethyl-5-(5-fluoropyrid-3-yl)pyrazine (430 mg, 13%) as a yellow solid. $^1$H NMR (400 MHz, CDCl$_3$) δ8.95 (s, 1H), 8.75 (s, 1H), 8.50 (s, 1H), 8.00 (d, 1H), 5.35 (br s, 2H).

Example P4: Preparation of tert-butyl N-(5-bromo-3-methyl-pyrazin-2-yl)-carbamate

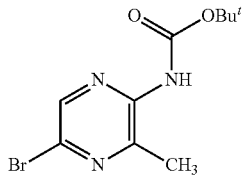

Step 1: Preparation of tert-butyl N-(3-methyl-pyrazin-2-yl)-carbamate

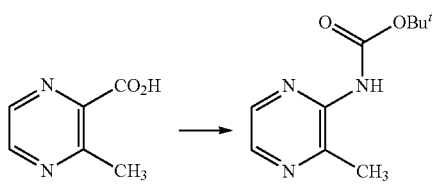

Diphenylphosphoryl azide (22.2 g, 80.5 mmol) was added to a stirred solution of 3-methylpyrazine-2-carboxylic acid (9.0 g, 61.9 mmol) in toluene (90 ml), tert-butanol (45 ml) and triethylamine (8.18 g, 80.5 mmol). The resulting mixture was heated at 90° C. for 4 hours (reaction was observed to begin during heating, at about 65° C. internal temperature) and then allowed to cool. The solvent was removed under reduced pressure and the residue was re-dissolved in ethyl acetate (150 ml). The resulting solution was washed with 2M aqueous sodium bicarbonate then dried using a phase separation membrane, concentrated under reduced pressure and purified by chromatography on silica gel using a gradient of ethyl acetate in hexane as eluent to give tert-butyl N-(3-methyl-pyrazin-2-yl)-carbamate (8.0 g, 59%) as a colourless oil which slowly crystallised.
$^1$H NMR (400 MHz CDCl$_3$) δ8.27 (d, 1H), 8.23 (d, 1H), 6.85 (br s, 1H), 1.53 (s, 9H).
Step 2: Preparation of N-(5-bromo-3-methyl-pyrazin-2-yl)-carbamate

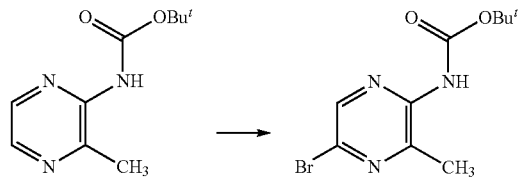

Bromine (127 mg, 0.79 mmol) was added dropwise at room temperature to a stirred solution of tert-butyl N-(3-methyl-pyrazin-2-yl)-carbamate (150 mg, 0.72 mmol) and pyridine (69 mg, 0.86 mmol) in chloroform (4.5 ml). The resulting mixture was stirred at room temperature for 24 hours and then concentrated under reduced pressure. The residue was dissolved in dichloromethane (10 ml), washed with water, dried using a phase-separation membrane and purified by chromatography on silica gel using mixtures of ethyl acetate and hexane as eluent to give tert-butyl N-(5-bromo-3-methyl-pyrazin-2-yl)-carbamate as a white solid (140 mg, 68%). $^1$H NMR (400 MHz, CDCl$_3$) δ8.30 (s, 1H) 6.65 (br s, 1H), 2.55 (s, 3H), 1.55 (s, 9H).

Example P5: Preparation of 3-trifluoromethyl-2-aminopyrazine

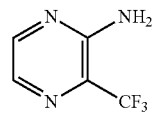

Step 1: Preparation of tert-butyl N-(3-trifluoromethylpyrazin-2-yl)-carbamate

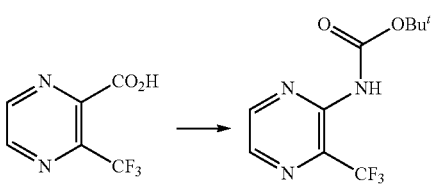

Diphenylphosphoryl azide (3.47 g, 12.6 mmol) was added to a stirred solution of 3-trifluoromethylpyrazine-2-carboxylic acid (1.92 g, 9.70 mmol) and triethylamine (1.28 g, 12.6 mmol) in tert-butanol (9.6 ml, 100 mmol) and toluene (19.2 ml). The resulting mixture was heated at 90° C. for 4 hours and then allowed to cool. It was washed with 2M aqueous sodium bicarbonate, then dried through a phase-separation filter and concentrated under reduced pressure. The residue was purified by chromatography on silica gel using a gradient of ethyl acetate in hexane as eluent to give tert-butyl N-(3-trifluoromethylpyrazin-2-yl)-carbamate containing 3-trifluoromethyl-2-aminopyrazine (2.0 g) as a colourless oil which slowly crystallised to give a white solid. $^1$H NMR (400 MHz, CDCl$_3$) δ8.70 (s, 1H), 8.40 (s, 1H), 7.20 (br s, 1H), 1.55 (s, 9H).
Step 2: Preparation of 3-trifluoromethyl-2-aminopyrazine

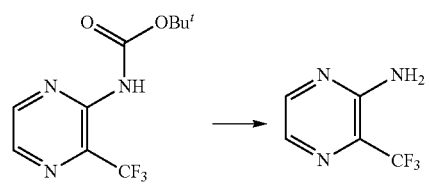

Trifluoroacetic acid (1.1 ml, 14 mmol) was added in portions to a stirred solution of the crude tert-butyl N-(3-trifluoromethylpyrazin-2-yl)-carbamate (0.92 g, ca. 3.5 mmol) in 1,2-dichlorethane (9.2 ml) at room temperature.

The resulting mixture was heated under reflux for 2 hours, allowed to cool, then washed with saturated aqueous sodium bicarbonate and dried through a phase-separation filter. Concentration under reduced pressure then gave 3-trifluoromethyl-2-aminopyrazine (0.48 g) as a yellow solid ¹H NMR (400 MHz, CDCl₃) δ8.25 (s, 1H), 8.00 (s, 1H), 5.15 (br s, 1H).

Example P6: Preparation of tert-butyl N-(3-methyl-pyrazin-2-yl)-N-methyl-carbamate

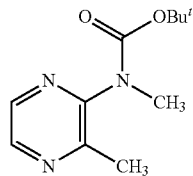

Step 1: Preparation of tert-butyl N-(3-methyl-pyrazin-2-yl)-N-methyl-carbamate

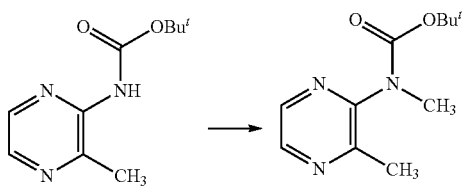

A solution of tert-butyl N-(3-methyl-pyrazin-2-yl)-carbamate (1.05 g, 5.0 mmol) in dry DMF was added dropwise to a stirred suspension of sodium hydride (220 mg, 5.5 mmol) in dry DMF at room temperature (total volume of DMF ~10 ml) (effervescence). The resulting mixture was stirred at room temperature for 30 minutes, then methyl iodide (3.6 g, 25 mmol) was added in one portion. The reaction mixture was stirred for 2 hours, then quenched with water and extracted with ethyl acetate. The extracts were washed with water and brine, then dried over magnesium sulfate and concentrated under reduced pressure. The residue was purified mass directed reverse phase HPLC to give tert-butyl N-(3-methyl-pyrazin-2-yl)-N-methyl-carbamate (24 mg, 2%) as an oil. ¹H NMR (400 MHz, CDCl₃) δ7.35 (d, 1H), 7.00 (d, 1H), 3.55 (s, 3H), 2.50 (s, 3H), 1.55 (s, 9H).

Example P7: Preparation of 2-amino-3-trifluoromethyl-5-bromopyrazine

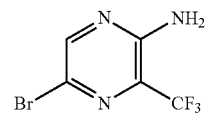

Step 1: Preparation of 2-amino-3-trifluoromethyl-5-bromopyrazine

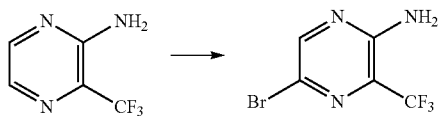

A solution of bromine in dichloromethane (10 ml) was added in portions to a stirred solution of 2-amino-3-trifluoromethylpyrazine (1.5 g, 9.2 mmol) and pyridine (0.90 ml, 11 mmol) in chloroform. The resulting mixture was stirred at room temperature for 24 hours. Volatiles were removed under reduced pressure and the residue was purified by chromatography on silica gel using a gradient of ethyl acetate in isohexane as eluent to give 2-amino-3-trifluoromethyl-5-bromopyrazine (1.7 g, 77% yield) as an off-white solid. ¹H NMR (400 MHz, CDCl₃) δ8.30 (s, 1H), 5.13 (br s, 2H).

Further examples of the invention can be prepared similarly using the methods described above. Table 2 below, shows the structure of these compounds and the physical characterising data obtained using one or more of methods as outlined below.

TABLE 2

Characterising data for Compounds of formula (I) made by the methods above.

| Compound ID | Structure | Data (400 MHz, CDCl₃) unless stated |
|---|---|---|
| I1 | 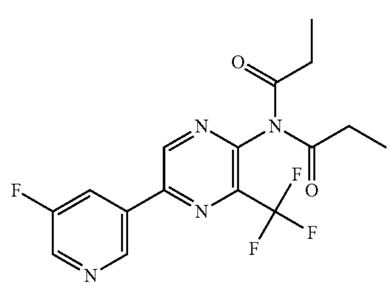 [SMILES: CCC(=O)N(C(=O)CC)c1ncc(-c2cncc(F)c2)nc1C(F)(F)F] | 9.30 (s, 1H), 9.15 (s, 1H), 8.70 (d, 1H), 8.20 (dd, 1H), 2.70-2.45 (m, 4H), 1.15 (t, 6H) |

TABLE 2-continued

Characterising data for Compounds of formula (I) made by the methods above.

| Compound ID | Structure | Data (400 MHz, CDCl₃) unless stated |
|---|---|---|
| I2 | 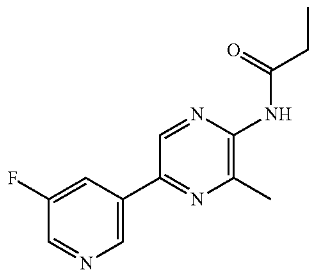 [SMILES: CCC(=O)Nc1ncc(-c2cncc(F)c2)nc1C] | 9.10 (s, 1H), 8.70 (s, 1H), 8.60 (d, 1H), 8.25 (dd, 1H), 7.80 (br s, 1H), 2.70-2.60 (m, 5H), 1.30 (t, 3H) |
| I3 | 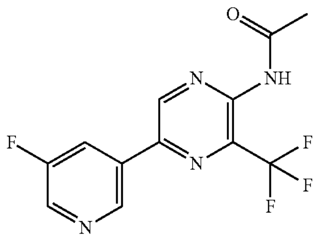 [SMILES: CC(=O)Nc1ncc(-c2cncc(F)c2)nc1C(F)(F)F] | 9.10 (s, 2H), 8.60 (s, 1H), 8.15 (dd, 1H), 7.85 (br s, 1H), 2.45 (s, 3H) |
| I4 | 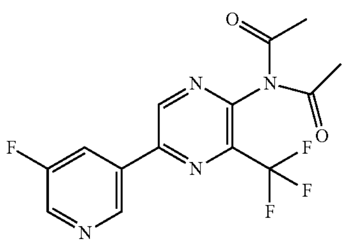 [SMILES: CC(=O)N(C(C)=O)c1ncc(-c2cncc(F)c2)nc1C(F)(F)F] | 9.30 (s, 1H), 9.15 (s, 1H), 8.70 (s, 1H), 8.25 (dd, 1H), 2.35 (s, 6H) |
| I5 | 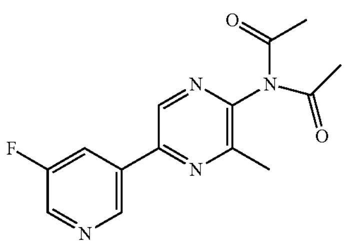 [SMILES: CC(=O)N(C(C)=O)c1ncc(-c2cncc(F)c2)nc1C] | 9.10 (s, 1H), 8.90 (s, 1H), 8.60 (s, 1H), 8.15 (dd, 1H), 2.60 (s, 3H), 2.30 (s, 6H) |
| I6 | 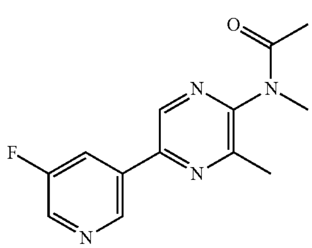 [SMILES: CC(=O)N(C)c1ncc(-c2cncc(F)c2)nc1C] | (major rotamer) 9.10 (br s, 1H), 8.85 (br s 1H), 8.60 (br s, 1H), 8.20 (dd, 1H), 3.30 (br s, 3H), 2.65 (br s, 3H), 1.90 (br s, 3H) |
| I8 | 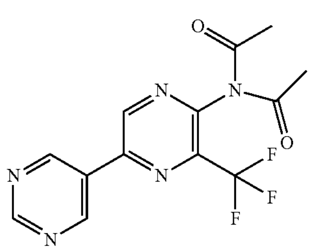 [SMILES: CC(=O)N(C(C)=O)c1ncc(-c2cncnc2)nc1C(F)(F)F] | 9.50 (s, 2H), 9.40 (s, 1H), 9.25 (s, 1H), 2.35 (s, 6H) |

TABLE 2-continued

Characterising data for Compounds of formula (I) made by the methods above.

| Compound ID | Structure | Data (400 MHz, CDCl$_3$) unless stated |
|---|---|---|
| I9 | 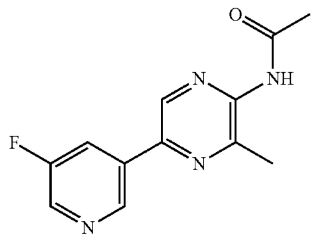 [SMILES: CC(=O)Nc1ncc(-c2cncc(F)c2)nc1C] | 9.05 (s, 1H), 8.70 (s, 1H), 8.55 (s, 1H), 8.20 (dd, 1H), 7.70 (br s, 1H), 2.65 (s, 3H), 2.40 (s, 3H) |
| I10 | 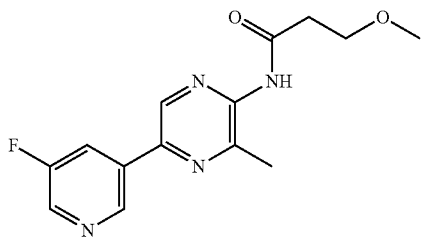 [SMILES: COCCC(=O)Nc1ncc(-c2cncc(F)c2)nc1C] | 9.10 (s, 1H), 8.90 (br s, 1H), 8.75 (s, 1H), 8.60 (d, 1H), 8.20 (dd, 1H), 3.80 (t, 2H), 3.50 (s, 3H), 2.80 (t, 2H), 2.6 (s, 3H) |
| I11 | 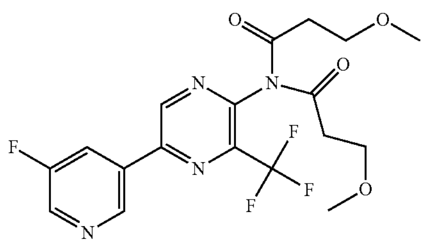 [SMILES: COCCC(=O)N(C(=O)CCOC)c1ncc(-c2cncc(F)c2)nc1C(F)(F)F] | 9.30 (s, 1H), 9.20 (s, 1H), 8.70 (d, 1H), 8.25 (dd, 1H), 3.70 (t, 4H), 3.35 (s, 6H), 2.95-2.75 (m, 4H) |
| I12 | 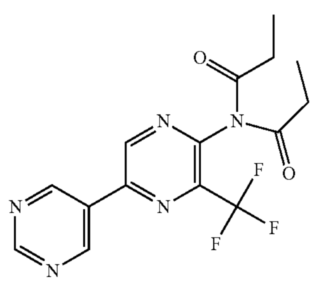 [SMILES: CCC(=O)N(C(=O)CC)c1ncc(-c2cncnc2)nc1C(F)(F)F] | 9.50 (s, 2H), 9.40 (s, 1H), 9.30 (s, 1H), 2.70-2.50 (m, 4H), 1.18 (t, 6H) |

Physical Characterisation

Compounds of the invention were characterised using one or more of the following methods.

NMR

NMR spectra contained herein were recorded on either a 400 MHz Bruker AVANCE III HD equipped with a Bruker SMART probe or a 500 MHz Bruker AVANCE III equipped with a Bruker Prodigy probe. Chemical shifts are expressed as ppm downfield from TMS, with an internal reference of either TMS or the residual solvent signals. The following multiplicities are used to describe the peaks: s=singlet, d=doublet, t=triplet, dd=double doublet, m=multiplet. Additionally br. is used to describe a broad signal and app. is used to describe and apparent multiplicity.

LCMS

LCMS data contained herein consists of the molecular ion [MH+] and the retention time (tr) of the peak recorded on the chromatogram. The following instruments, methods and conditions were used to obtain LCMS data:

Method A

Instrumentation: Waters Acquity UPLC-MS using a Sample Organizer with Sample Manager FTN, H-Class QSM, Column Manager, 2×Column Manager Aux, Photodiode Array (Wavelength range (nm): 210 to 400, ELSD and SQD 2 equipped with a Waters HSS T3 C18 column (column length 30 mm, internal diameter of column 2.1 mm, particle size 1.8 micron).

Ionisation method: Electrospray positive and negative: Capillary (kV) 3.00, Cone (V) 30.00, Source Temperature (° C.) 500, Cone Gas Flow (L/Hr.) 10, Desolvation Gas Flow (L/Hr.) 1000. Mass range (Da): positive 95 to 800, negative 115 to 800.

The analysis was conducted using a two minute run time, according to the following gradient table at 40° C.:

| Time (mins) | Solvent A (%) | Solvent B (%) | Flow (ml/mn) |
|---|---|---|---|
| 0.00 | 95.0 | 5.0 | 0.7 |
| 1.75 | 0.0 | 100 | 0.7 |
| 1.76 | 0.0 | 100 | 0.7 |
| 2.0 | 0.0 | 5.0 | 0.7 |
| 2.01 | 95.0 | 5.0 | 0.7 |
| 2.11 | 95.0 | 5.0 | 0.7 |

Solvent A: $H_2O$ with 0.05% TFA
Solvent B: $CH_3CN$ with 0.05% TFA

Method B (2 min Method)
Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).
LC-Method:
Phenomenex 'Kinetex C18 100A' column (50 mm×4.6 mm, particle size 2.6 micron), Flow rate: 2 mL/min at 313K (40 Celsius),
Gradient (Solvent A: $H_2O$ with 0.1% Formic Acid; Solvent B: Acetonitrile with 0.1% Formic Acid):
The analysis was conducted using a two minute run time, according to the following gradient table at 40° C.

| Time (mins) | Solvent A (%) | Solvent B (%) | Flow (ml/mn) |
|---|---|---|---|
| Initial | 70.0 | 30.0 | 2.000 |
| 1.20 | 10.0 | 90.0 | 2.000 |
| 1.70 | 10.0 | 90.0 | 2.000 |
| 1.80 | 70.0 | 30.0 | 2.000 |
| 2.00 | 70.0 | 30.0 | 2.000 |
| 2.20 | 70.0 | 30.0 | 2.000 |

Method C (1 min Method)
Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).
LC-Method:
Phenomenex 'Kinetex C18 100A' column (50 mm×4.6 mm, particle size 2.6 micron), Flow rate: 2 mL/min at 313K (40 Celsius),
Gradient (Solvent A: $H_2O$ with 0.1% Formic Acid; Solvent B: Acetonitrile with 0.1% Formic Acid):
The analysis was conducted using a one minute run time, according to the following gradient table at 40° C.

| Time (mins) | Solvent A (%) | Solvent B (%) | Flow (ml/mn) |
|---|---|---|---|
| Initial | 60.0 | 40.0 | 2.000 |
| 0.80 | 0.0 | 100.0 | 2.000 |
| 0.95 | 0.0 | 100.0 | 2.000 |
| 1.00 | 60.0 | 40.0 | 2.000 |
| 1.10 | 60.0 | 40.0 | 2.000 |
| 1.25 | 60.0 | 40.0 | 2.000 |

BIOLOGICAL EXAMPLES

B1 Pre-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), and *Setaria faberi* (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B1.

TABLE B1

Control of weed species by compound of Formula (I) after pre-emergence application

| Compound ID | Rate (g/ha) | ECHCG | LOLPE | SETFA | AVEFA | ALOMY | TRAZW |
|---|---|---|---|---|---|---|---|
| I1 | 1000 | 2 | 1 | 3 | 1 | 0 | 0 |
| I2 | 1000 | 2 | 0 | 3 | 0 | 0 | 0 |
| I3 | 1000 | 3 | 0 | 4 | 1 | 0 | 0 |
| I4 | 1000 | 3 | 0 | 4 | 1 | 0 | 3 |
| I5 | 1000 | 2 | 1 | 3 | 0 | 0 | 0 |
| I6 | 1000 | 3 | 0 | 5 | 1 | 0 | 0 |
| I8 | 1000 | 2 | 1 | 4 | 0 | 0 | 0 |
| I9 | 1000 | 1 | 0 | 4 | 0 | 0 | 0 |
| I10 | 1000 | 2 | 0 | 2 | 0 | 0 | 0 |
| I11 | 1000 | 3 | 0 | 4 | 0 | 0 | 1 |
| I12 | 1000 | 2 | 0 | 3 | 1 | 0 | 0 |

B2 Post-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), and *Setaria faberi* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B2.

TABLE B2

Control of weed species by compound of Formula (I) after post-emergence application

| Compound ID | Rate (g/ha) | ECHCG | LOLPE | SETFA | AVEFA | ALOMY | TRAZW |
|---|---|---|---|---|---|---|---|
| I1 | 1000 | 4 | 1 | 4 | 2 | 0 | 0 |
| I2 | 1000 | 4 | 0 | 4 | 1 | 0 | 0 |
| I3 | 1000 | 3 | 1 | 4 | 3 | 1 | 1 |
| I4 | 1000 | 3 | 1 | 4 | 2 | 0 | 0 |
| I5 | 1000 | 2 | 1 | NT | 1 | 0 | 1 |
| I6 | 1000 | 4 | 2 | 5 | 3 | 1 | 1 |
| I7 | 1000 | 2 | 1 | 4 | 1 | 0 | 0 |
| I8 | 1000 | 4 | 1 | 5 | 2 | 1 | 1 |
| I9 | 1000 | 2 | 0 | 3 | 2 | 0 | 0 |
| I10 | 1000 | 3 | 0 | 2 | 1 | 0 | 0 |
| I11 | 1000 | 5 | 1 | 5 | 4 | 0 | 1 |
| I12 | 1000 | 3 | 1 | 4 | 2 | 1 | 1 |

The invention claimed is:

1. A compound of formula (I)

(I)

or a salt thereof,
wherein:
$X^1$ is N or $CR^1$;
$R^1$ is selected from the group consisting of halogen and cyano;
$R^2$ is selected from the group consisting of halogen, cyano, $C_1$-$C_6$alkyl and $C_1$-$C_6$haloalkyl;
$R^3$ is —C(O)$C_1$-$C_6$alkyl, or —C(O)$C_1$-$C_3$alkoxy$C_1$-$C_3$alkyl;
$R^4$ is selected from the group consisting of hydrogen, $C_1$-$C_4$alkyl, $C_1$-$C_3$haloalkyl and —C(O)$R^9$;
each $R^9$ is independently selected from the group consisting of hydrogen, methyl, ethyl, propyl, butenyl, —$C_1$-$C_3$alkoxy$C_1$-$C_3$alkyl, and —$(CH_2)_2C(O)OR^c$; and
$R^c$ is hydrogen or $C_1$-$C_4$alkyl.

2. The compound of formula (I) according to claim 1, wherein $X^1$ is N.

3. The compound of Formula (I) according to claim 1, wherein $X^1$ is $CR^1$ and $R^1$ is selected from the group consisting of fluoro, chloro, and cyano.

4. The compound of Formula (I) according to claim 1, wherein $R^2$ is cyano, methyl or trifluoromethyl.

5. The compound of Formula (I) according to claim 1, wherein $R^4$ is —C(C)$R^9$.

6. The compound of Formula (I) according to claim 1, wherein $R^4$ is hydrogen or methyl.

7. A herbicidal composition comprising a compound of Formula (I) as defined in claim 1 and an agriculturally acceptable formulation adjuvant.

8. The herbicidal composition according to claim 7, further comprising at least one additional pesticide.

9. A method of controlling grassy weeds at a locus comprising application to the locus of a grassy weed controlling amount of a compound of formula (I) as defined in claim 1.

10. A compound selected from the group consisting of:

-continued
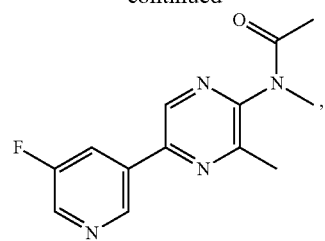
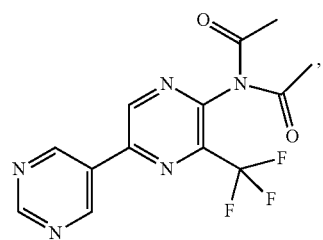
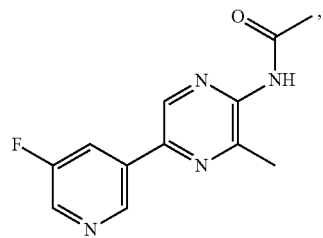
-continued
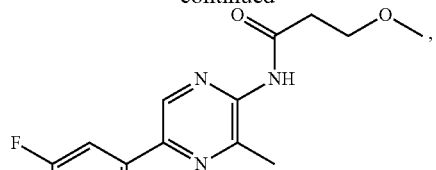
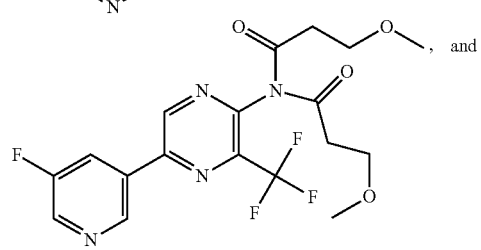
, and
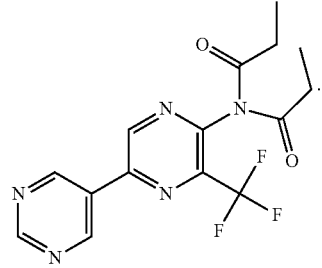
* * * * *